(12) United States Patent
Cao

(10) Patent No.: US 6,279,377 B1
(45) Date of Patent: Aug. 28, 2001

(54) METHOD AND APPARATUS FOR MONITORING OXYGEN CONCENTRATION

(75) Inventor: Tuan Q. Cao, Davenport, IA (US)

(73) Assignee: Litton Systems, Inc., Woodland Hills, CA (US)

(*) Notice: Subject to any disclaimer, the term of this patent is extended or adjusted under 35 U.S.C. 154(b) by 0 days.

(21) Appl. No.: 09/192,211

(22) Filed: Nov. 16, 1998

(51) Int. Cl.$^7$ .................. G01N 33/497; G01N 21/00; G01N 27/26; A61L 9/00
(52) U.S. Cl. .................. 73/23.31; 73/863.81; 73/1.06; 422/3; 204/401
(58) Field of Search .................. 73/23.31, 863.81, 73/1.06; 422/3, 4; 204/401

(56) References Cited

U.S. PATENT DOCUMENTS

| | | |
|---|---|---|
| 4,189,725 | 2/1980 | Rowland . |
| 4,390,869 | 6/1983 | Christen et al. . |
| 4,464,653 | 8/1984 | Winner . |
| 4,779,446 | 10/1988 | Rowland . |
| 4,852,384 * | 8/1989 | Woolbert et al. .................. 73/1.07 |
| 5,198,774 * | 3/1993 | Williams, II et al. .................. 324/468 |
| 5,402,665 | 4/1995 | Hart et al. . |
| 5,423,963 * | 6/1995 | Fletcher et al. .................. 205/782.5 |
| 5,623,105 * | 4/1997 | Liston et al. .................. 73/863.81 |

* cited by examiner

Primary Examiner—Hezron Williams
Assistant Examiner—Jay L. Politzer
(74) Attorney, Agent, or Firm—Lowe Hauptman Gilman & Berner, LLP

(57) ABSTRACT

Apparatus for measuring concentration of oxygen includes a plurality of status displays, identifying concentration status relative to a plurality of thresholds, an alarm for immediate and prominent identification of status relative to a threshold of particular significance, and a quantitative display indicative of an actual concentration. Although measurements are performed and results are indicated relative to a number of thresholds, only a single calibration procedure is required, using only a single calibration gas. The apparatus is calibrated by adjusting a circuit parameter of one of the circuit components to vary a sensed output value to correspond to a narrow range surrounding the known concentration of the calibration gas. Both the circuit parameter and the actually sensed output value are stored. In a monitoring operation, the circuit parameter is retrieved to reset the circuit component to its calibrated setting. The monitored unknown value of concentration is scaled based on a value in a look-up table and on the actually sensed output value of the calibration process. An interpolation between values of the look-up table is then used to identify a concentration corresponding to the scaled value.

18 Claims, 7 Drawing Sheets

| FIG. 2A | FIG. 2C |
| FIG. 2B | FIG. 2D |

METHOD AND APPARATUS FOR MONITORING OXYGEN CONCENTRATION

TECHNICAL FIELD

This invention relates generally to comparison of concentration of a gas with a threshold, and more particularly to monitoring of oxygen concentration and annunciating results of such monitoring for plural thresholds and values, using only a single calibration concentration.

BACKGROUND ART

Hazards of excessive or inadequate concentration of specific gases exist in many forms. For example, low oxygen levels may lead to asphyxiation. On the other hand, excessive oxygen levels may create a combustion hazard. However, various industrial processes require large amounts of liquid or gaseous nitrogen and oxygen. Thus, in the home health care environment, it is desirable to monitor the output of an oxygen concentrator to determine whether the output oxygen level remains above (or falls below) a predetermined minimum desired limit. In other industrial and commercial applications, it is desirable to maintain oxygen concentration between preset lower and upper limits.

Accordingly, the presence or absence of oxygen or other gaseous materials, in concentrations having specific relationships to predefined thresholds, may create a potential for serious problems.

Thus, as a safety precaution, every situation wherein excessively low or excessively high concentrations of gases (such as oxygen) may exist, requires identification and evaluation of the specific concentration. For example, a long stretch of hallway with high pressure gas lines; a room with poor ventilation and significant amounts of inert or oxygen rich gas storage, or an environment having storage areas for chemicals which can deplete or enrich the oxygen concentration therein, provide potentially hazardous environments which should be monitored.

When an oxygen hazard may exist, there is needed a drift free, long life, accurate and dependable oxygen monitoring devices.

Oxygen concentration monitors are known in the prior art. For example, one such apparatus is disclosed in U.S. Pat. No. 5,402,665 to Hart et al., the contents of which are incorporated herein by reference.

However, the apparatus disclosed therein operates to compare ambient oxygen concentration with a predetermined threshold level and to provide an indication when the monitored concentration exceeds (or falls below) the threshold. More particularly a calibration gas, having an oxygen concentration equal to a desired threshold concentration level, is used to calibrate the device in order to account for variations in the operating characteristics of the oxygen sensor used therein. A specific testing and calibration procedure is thus required and the disclosed apparatus provides an indication if the monitored concentration is greater (or less) than the desired threshold.

The patent also discloses that one or more calibration gases may be used, at respective concentrations, in order to establish various calibration threshold levels.

However, a drawback of such a device is that a plurality of specific calibration procedures must be followed in order to calibrate the device to monitor concentrations with respect to a plurality of threshold levels to be monitored. Moreover, while the disclosed device may activate an audible alarm, buzzer, or LED (light emitting diode) to indicate a relationship between the concentration being monitored and a threshold, there is no provision for indicating the actual oxygen concentration level.

There is thus a need in the prior art for method and apparatus for monitoring concentrations of oxygen using only a single calibration gas.

DISCLOSURE OF INVENTION

It is accordingly an object of the present invention to provide a method and apparatus for monitoring concentration of oxygen using only a single calibration gas.

More specifically, it is an object of the invention to provide improved methods and apparatus for using a single calibration procedure, with a single calibration gas, for monitoring concentration of oxygen relative to a plurality of thresholds.

It is a particular object of the invention to provide an accurate display of the oxygen concentration level in a wide range of concentrations, following a single calibration procedure with a single calibration gas.

It is a more specific object of the invention to provide an oxygen concentration monitor, providing an indication of oxygen concentration relative to a plurality of thresholds, which requires only a single calibration procedure.

It should be appreciated, however, that while the disclosure refers specifically to monitoring of oxygen, the techniques described herein may be used for accurately sensing and monitoring concentrations of other gases.

In accordance with the invention, there is thus provided an oxygen monitoring apparatus which stores parameters descriptive of the operating characteristics of an oxygen sensor used therein for a calibration gas having a particular concentration, and which retrieves the parameters to determine the concentration of oxygen relative to any threshold concentration.

In accordance with another aspect of the invention, there is provided an oxygen monitoring apparatus which retrieves stored parameters descriptive of operating characteristics of an oxygen sensor and which uses the retrieved parameters in conjunction with other stored data to determine the concentration of oxygen being monitored.

In accordance with still another feature of the invention, there are provided a method and apparatus for identifying a monitored oxygen concentration level by determining a value necessary to compensate for characteristics of an oxygen sensor in a predetermined concentration of oxygen, by obtaining an output value from the sensor in an unknown concentration of oxygen, by modifying the output value to compensate for the sensor characteristics using the determined value, and by using the compensated value in conjunction with a table identifying expected sensor output values to identify the monitored concentration level.

These and other objects, features and advantages of the present invention will become readily apparent to those skilled in the art from the following description and drawings, wherein there is shown and described a preferred embodiment of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWING

The accompanying drawings, incorporated into and forming a part of the specification, illustrate several aspects of a preferred embodiment of the present invention and, together with the description, serve to explain the principles of the invention. In the drawings.

BEST MODE FOR CARRYING OUT THE INVENTION

Figure 1:
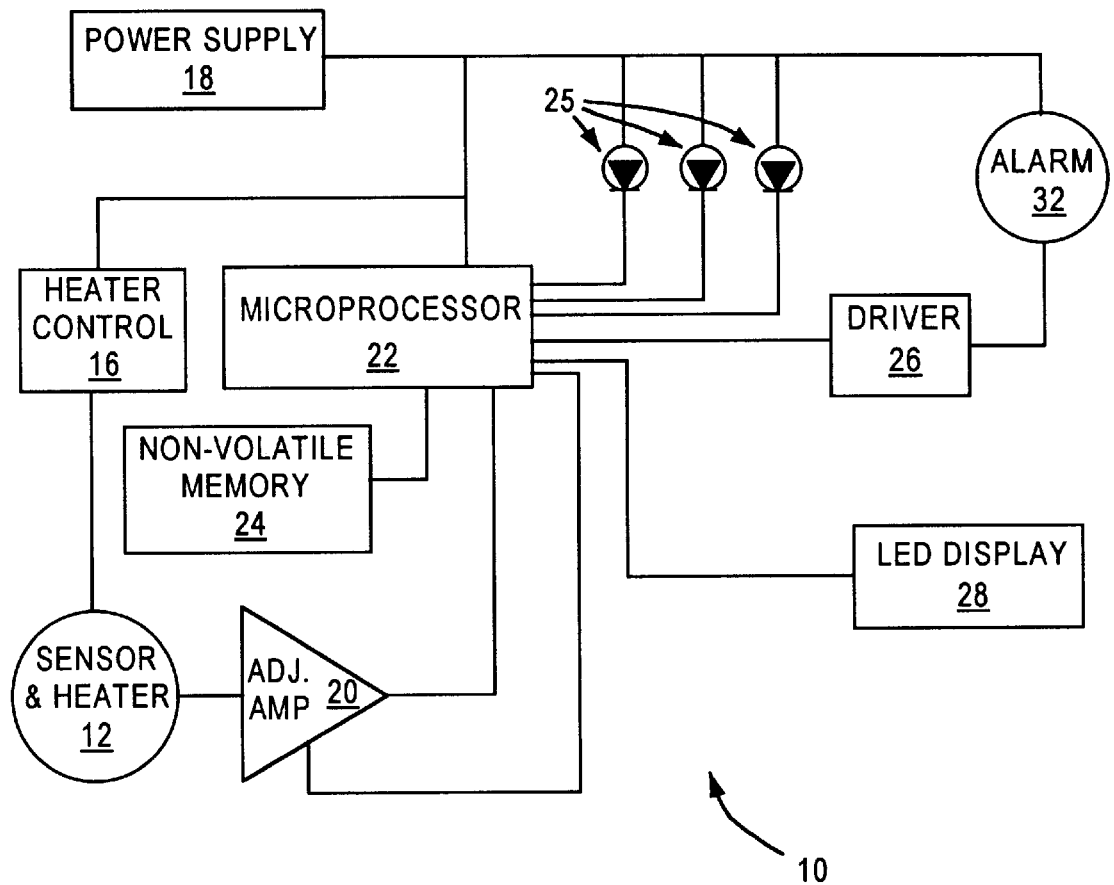
FIG. 1 is a block diagram depicting a gas concentration monitor in accordance with the invention.

Referring now to the drawings, in FIG. 1 there is shown a block diagram representation of an oxygen monitor 10 embodying the concepts of the invention. The broad concepts of an oxygen monitor structure do not form a part of the invention and may be appreciated from the description of previously referenced U.S. Pat. No. 5,402,665. Thus, it is known that monitor 10 includes an oxygen sensor and heater unit 12, the heater being controlled by a heater control 16. A power supply 18 provides electrical power to the monitor and the various components thereof.

Of significance to the invention, there is provided an adjustable amplifier 20, having a variably adjustable gain. The gain of amplifier 20 is controlled by a microprocessor 22 which also receives the output of the amplifier. As will be further described hereinbelow, the gain setting used during a calibration procedure is also received by microprocessor 22, and is stored in a non-volatile memory 24, which may also be used to store the operating program controlling microprocessor 22, as well as other data.

In operation, when oxygen concentration is being monitored, the output of the sensor 12 is amplified by amplifier 20 and is received by microprocessor 22. Upon evaluating the amplifier output, microprocessor 22 may activate respective ones of a plurality of status LED=s 25 to indicate the relationship between the sensed concentration of oxygen and any of a plurality of respective threshold values. Alternatively, or concurrently, microprocessor 22 may control a driver 26 to activate an alarm 32 in the event that the monitored concentration has a particular relationship to a particularly significant threshold. Moreover, microprocessor 22 may cause a value of the oxygen concentration, as represented by the output of sensor 12 as amplified by the adjustable gain amplifier 20, to be displayed on a LED display 28 or other display, thereby to provide a numerical representation of the concentration level.

Figures 2, 2A:
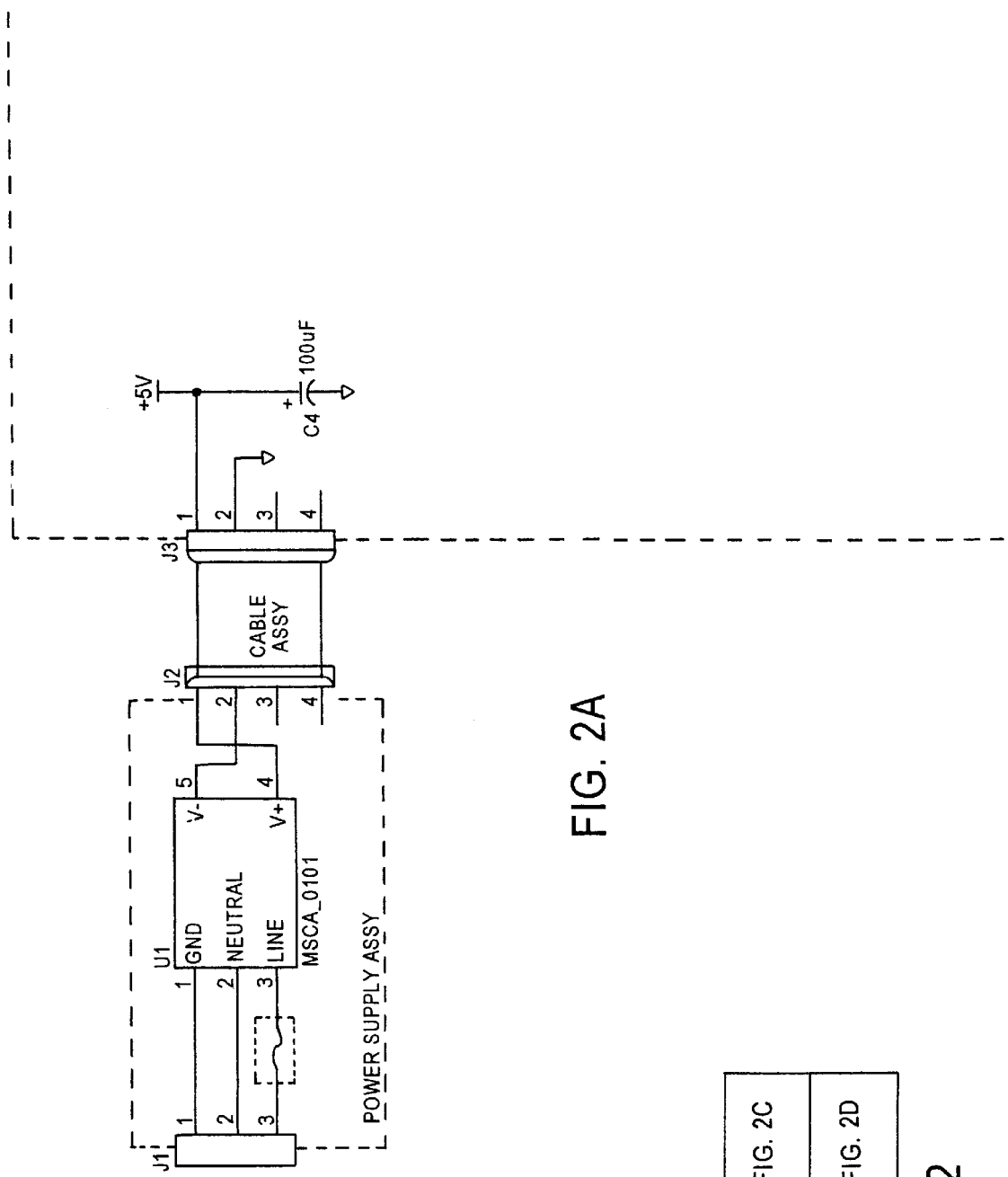
FIG. 2 is a detailed schematic diagram of an embodiment of the inventive concept illustrated in FIG. 1.
Figure 2B:
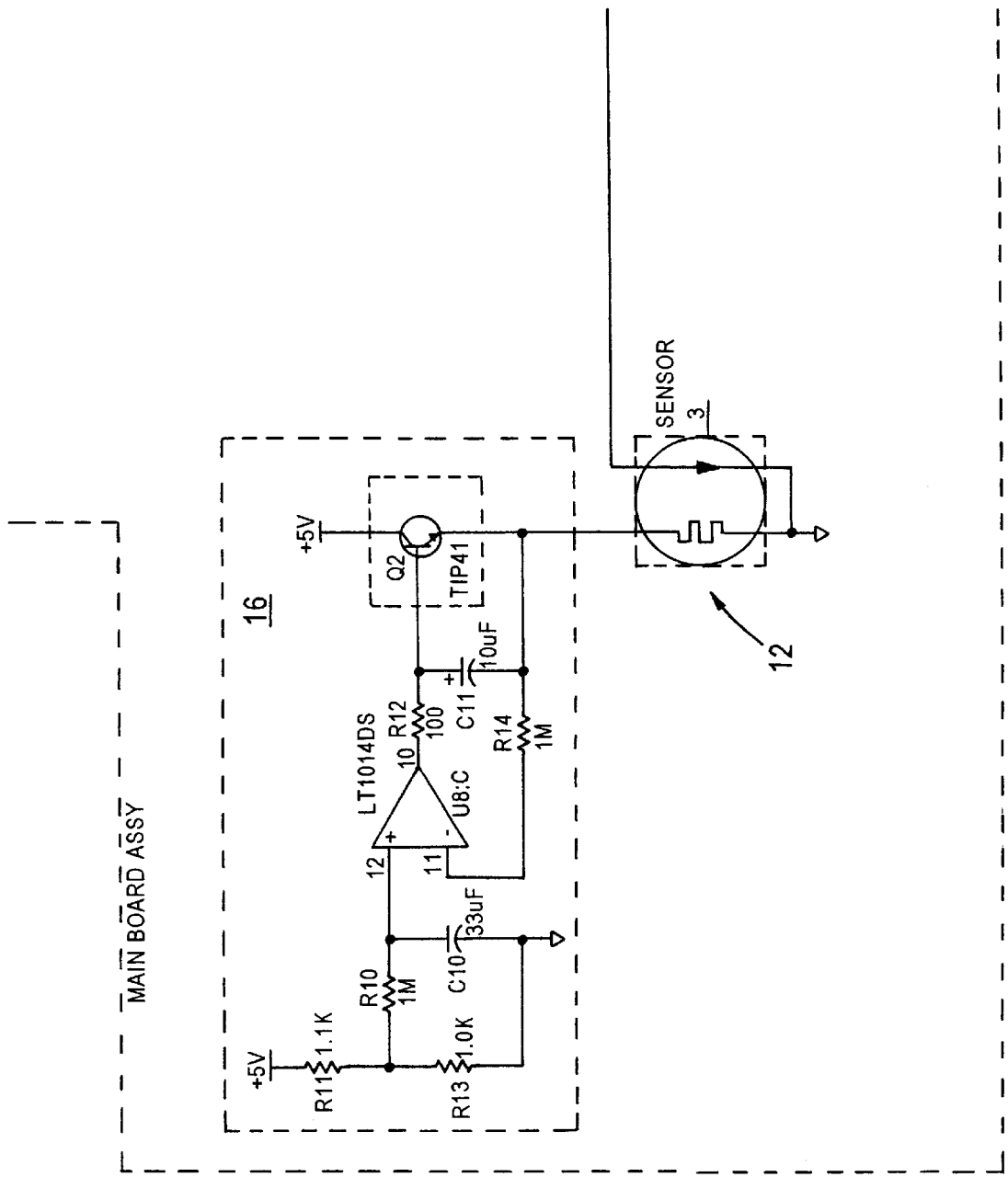
Figure 2C:
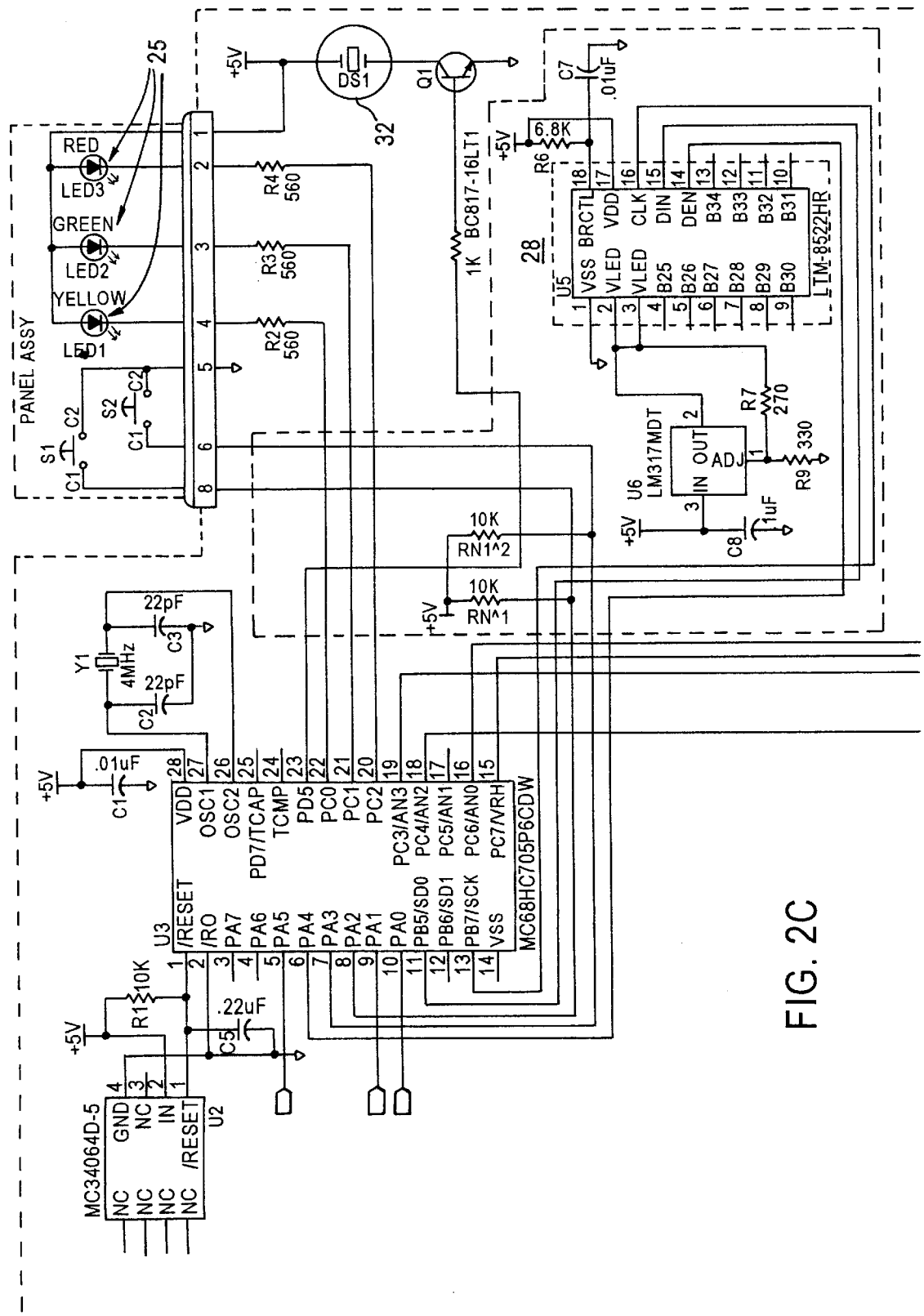
Figure 2D:
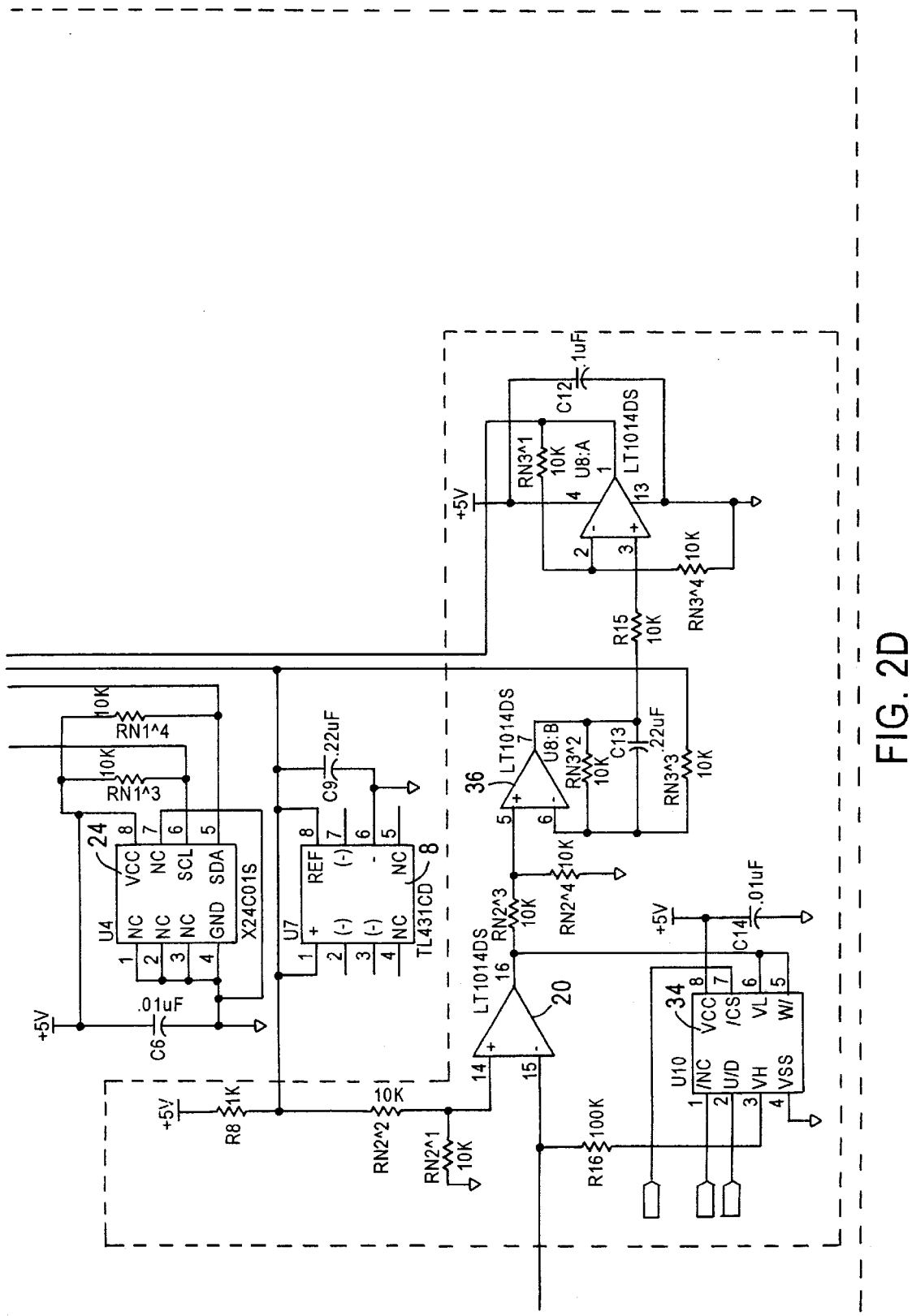

Referring to FIG. 2, it will be appreciated that heater control 16 is used to control the heater portion of the sensor and heater unit 12. The output of the sensor in unit 12 is provided to variable gain amplifier 20, whose gain is controlled by an EEPOT (electrically erasable potentiometer) 34. The output of amplifier 20, after passing through a bias subtractor stage 36, is provided to microprocessor 22.

Microprocessor 22 may be any known 8-bit processor, with an on-board analog-to-digital converter (ADC). One such device is commercially available from Motorola under the designation MC68HC705P6CDW. Block 38 provides a voltage reference for bias subtractor 36. As will be appreciated upon reference to the flow chart of FIG. 3, during a calibration procedure microprocessor 22 stores the setting of EEPOT 34, which represents the gain value of adjustable gain amplifier 20, in non-volatile memory 24. Of course, the 8-bit microprocessor shown in FIG. 2 is provided only as an illustration of the inventive concept and any other microprocessor suitable for implementing the functions and concepts described herein may be used in its stead.

Figure 3:
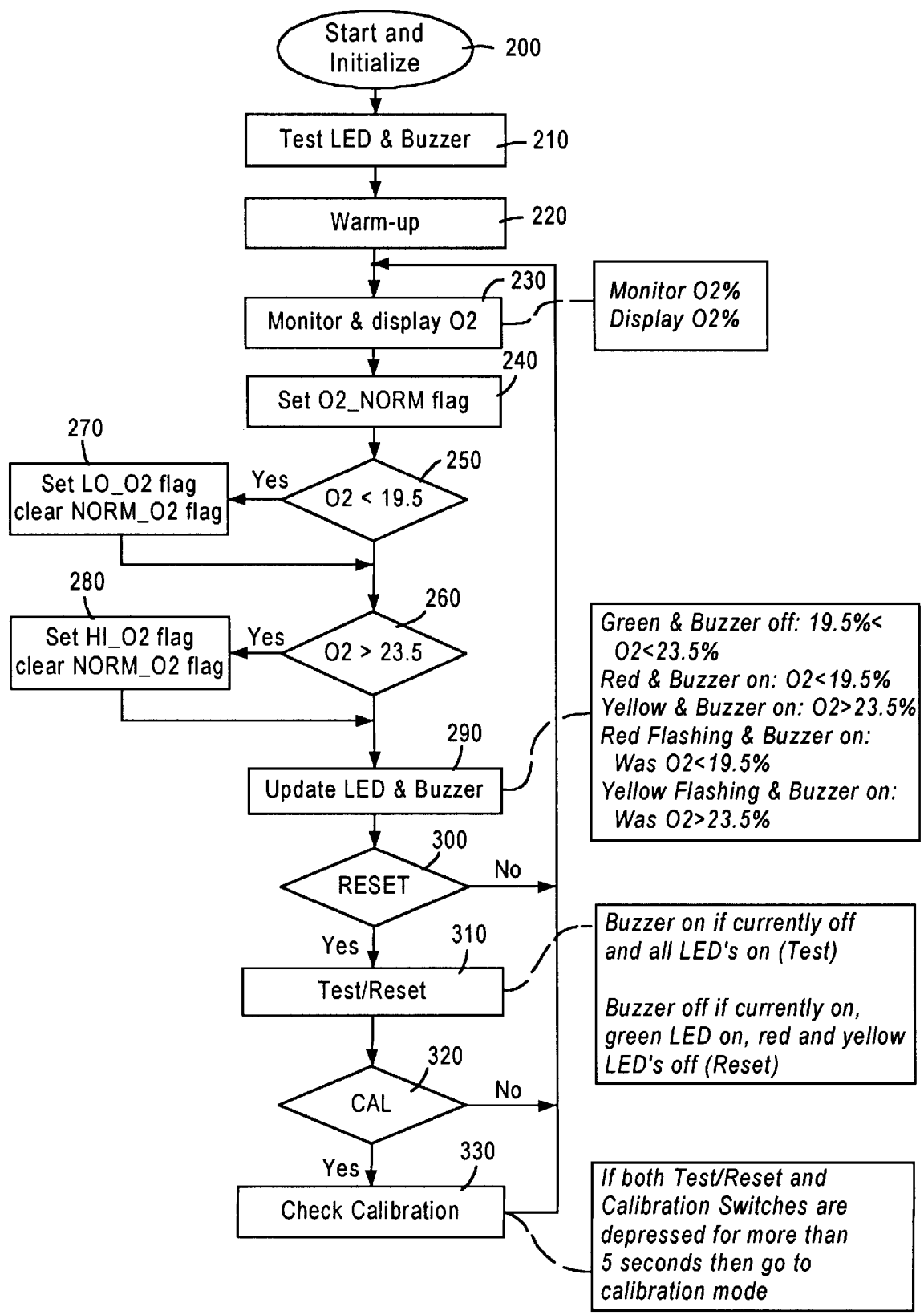
FIG. 3 is a flow chart describing operation of the invention illustrated in FIGS. 1 and 2.

Referring now to FIG. 3, system operation begins at a step 200. Such operation may begin in response to activation of a "start" switch, or other input or command from a user or from another apparatus. As part of the start operation, the microprocessor initializes the system as follows.

A digitally converted value of the EEPOT setting, obtained during a calibration process and representing the calibration value for the oxygen sensor, is retrieved from the non-volatile memory 24. Microprocessor 22 then restores EEPOT 34 to the setting corresponding to the retrieved value, thus providing the appropriate gain setting for variable gain amplifier 20 previously determined in a calibration procedure. At a step 210 the microprocessor tests operation of the various LED's 25, buzzer 32, and display 28, as well as any other output device which may be provided.

During the testing step 210, the LED display 28, as well as the various concentration status LED's 25 (representing the level of oxygen concentration with respect to various thresholds) will illuminate for a predetermined period of time, such as 3 seconds, and the audible alarm will similarly sound for a predetermined time period (such as 2 seconds) to indicate the normal start-up procedure. Thereafter, at a step 220, a warm-up procedure is implemented so that heater control 16 permits the heater in unit 12 to reach an appropriate temperature for proper operation of the oxygen sensor therein. The warm-up period may last approximately 240 seconds, during which a count-down is displayed on LED display 28, for example by counting down from 240 to 0, or by providing any other display such as a rotating indicator or the like. At a step 230, normal processing is implemented wherein the oxygen concentration is monitored by unit 12 in a known manner.

At that time, there is performed a linear interpolation between sensor output values and corresponding oxygen concentrations (which may be stored as a look-up table in non-volatile memory 24) in order to obtain the oxygen concentration represented by the actual output of the sensor in unit 12. The oxygen concentration corresponding to the output signal of the sensor may then be displayed on display 28. Additionally, the relationship between the determined concentration and any of a plurality of thresholds may be indicated by operation of various ones of LED's 25 and/or by operation of alarm 32. It should be appreciated that, while linear interpolation is described for illustrative purposes, identification of an oxygen concentration value corresponding to a sensor output value between two data points of the look-up table may be implemented in any known manner.

In one example of an embodiment of the present invention, LED's 25 may provide three differently colored indicia to represent oxygen concentration in three different ranges. The first LED may be of a red color and may be illuminated when the detected oxygen concentration is below 19.5%, representing an oxygen deficient environment. Under this condition of oxygen deficiency, microprocessor 22 may also activate alarm 32 to provide an audible alarm. A second LED may provide illumination of a green color and may represent a normal level of oxygen concentration, in the range of 19.5% to 23.5%. A third LED may provide yellow illumination to represent oxygen concentrations in excess of 23.5%, representing an oxygen enriched environment. Microprocessor 22 may also activate alarm 32 when the detected oxygen concentration is in excess of 23.5%.

Various of the above described functions of the system are summarized in the flow chart of FIG. 3 as follows. After setting an "O2-NORM" flag at step 240, a check is made at step 250 for an oxygen deficient condition. If it is determined that the oxygen concentration being monitored is below 19.5%, operation proceeds to step 270, where a "LO-O2" flag is set and the O2-NORM flag is cleared. The LO-O2 flag may be detected by microprocessor 22 and be used to cause illumination of the LED indicating an oxygen deficient environment, as well as to cause sounding of the alarm 32, in a known manner.

Whether the O2-NORM or the LO-O2 flag is set, operation proceeds to step 260. At this step, a check is made for an oxygen enriched condition. If it is determined that the oxygen concentration being monitored is above 23.5%, operation proceeds to step 280, where a "HI-O2" flag is set and the O2-NORM flag is cleared. The HI-O2 flag may be used to cause illumination of the LED indicating an oxygen enriched environment, as well as to cause sounding of the alarm 32.

At step 290, the appropriate LED is illuminated, depending on which of the O2-NORM, LO-O2 or HI-O2 flag is set. Thus, for oxygen concentrations between 19.5% and 23.5%, the green LED is illuminated, and the buzzer alarm is OFF. For concentrations below 19.5%, the red LED is illuminated and the buzzer alarm is turned ON. For concentrations above 23.5%, the yellow LED is illuminated and the buzzer alarm is turned ON. On the other hand, when the monitor detects that either an oxygen deficient or oxygen enriched environment has been corrected, and the currently detected concentration is in the acceptable range of 19.5% to 23.5%, there is provided an indication to alert a user and thus to permit a determination of whether the condition has changed or a system condition has changed.

More specifically, the red LED is caused to flash, with sounding of the buzzer alarm, following return to the normal concentration after detection of an oxygen deficient condition, while the yellow LED is caused to flash with sounding of the alarm following return to the normal concentration after detection of an oxygen enriched condition.

At step 300 it is determined whether the user has activated a "RESET" switch, key, or button, to initiate a reset procedure. If not, operation returns to step 230 where monitoring continues as above described. However, upon detection of activation of a RESET input, the system implements a test/reset procedure at step 310 followed by a calibration at step 330 if a calibration switch has been activated, as determined by a test thereof at step 320. Both a negative result of the test at step 320 and a conclusion of the calibration procedure at step 330 returns the microprocessor to implementation of the monitoring procedure at step 230.

The test/reset button of the monitor may be used at any time to verify proper display and alarm functions of the device. During the test/reset procedure of step 310, all status LED's 25 are activated, all segments of the display 28 are illuminated, and the buzzer alarm is activated. If the buzzer alarm is ON when the test/reset button is activated, microprocessor 22 turns the buzzer OFF. Following an alarm condition, pressing the test/reset button resets the alarm functions to normal operating conditions. That is, microprocessor 22 turns the green LED ON, and turns OFF (i.e., resets) the red and yellow LED's. This requires the ambient oxygen concentration to return to the 19.5% to 23.5% oxygen range.

More particularly, if the oxygen concentration returns to the normal range following an alarm condition, the status LED representing the particular out of range concentration status will begin to flash, the audible alarm will remain on, and the green status LED will illuminate. This condition continues until operation of the test/reset button, thus assuring that an operator is alerted to the fact that an alarm condition had previously existed in the area and that the cause thereof should be investigated.

Figure 4:
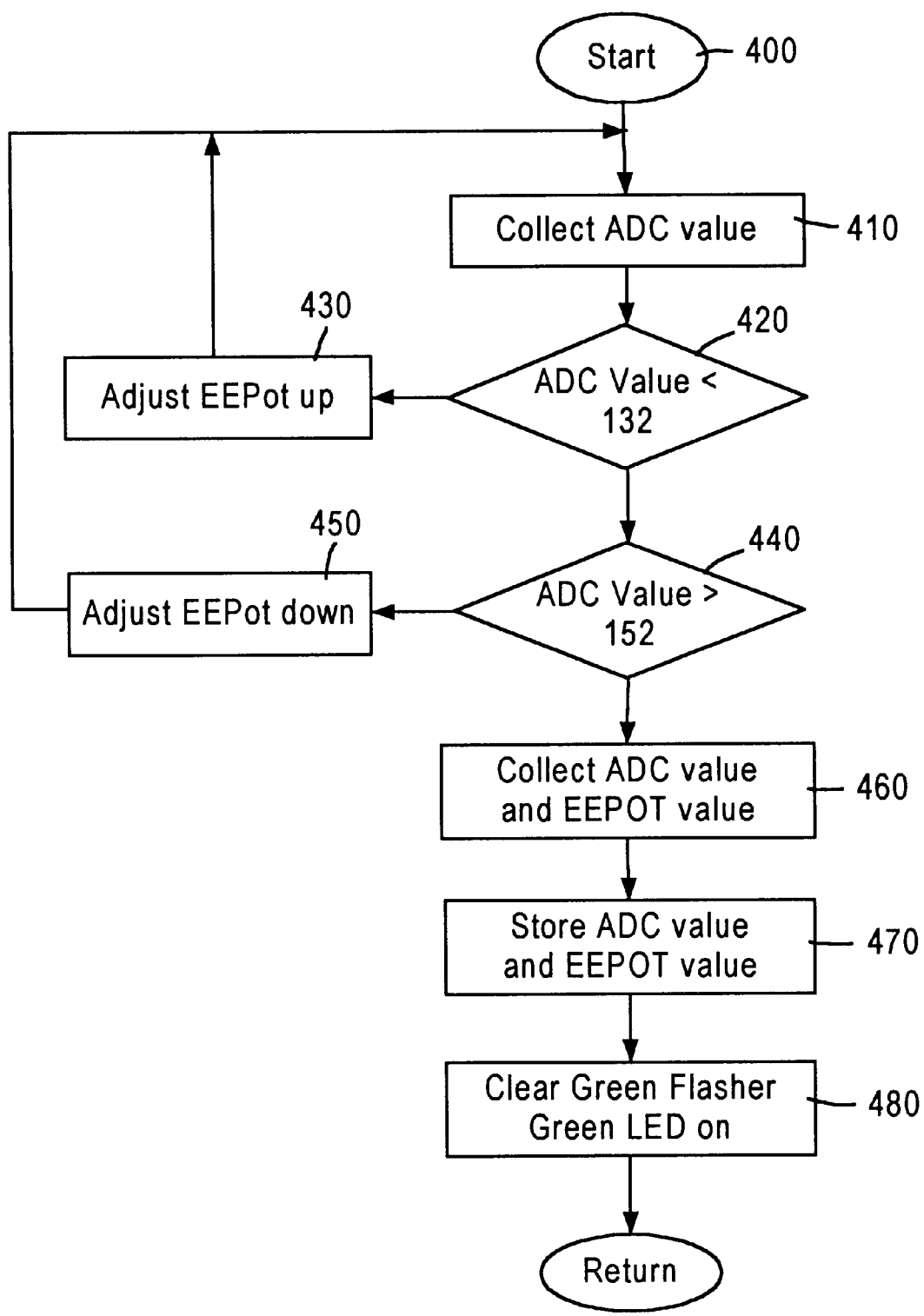
FIG. 4 is a flow chart describing a calibration procedure for the invention.

Referring now to the flow chart of FIG. 4, the calibration procedure implemented at step 320 is shown in more detail.

In accordance with the presently preferred embodiment of the invention, calibration is initiated by simultaneous operation of the calibration and the test/reset buttons for a predetermined period, such as 5 seconds. During this 5 second waiting period, LED display 28 indicates rotating segments. Then, the green LED is caused to flash and display 28 indicates the word "CAL" or other indication of calibration. At that time, upon releasing the calibration and test/reset buttons, the calibration process is implemented as follows.

As shown in FIG. 4, once calibration is started at a step 400, whether in response to activation of the calibration and test/reset switches by the user or in response to a system initiated calibration in accordance with a predetermined condition, and the calibration gas is provided to the sensor, the ADC value of the output of amplifier 20 is obtained at step 410. Steps 420–450 are used to vary the setting of EEPOT 34, and thus the gain of the variable gain amplifier 20, to a value which normalizes the output of sensor unit 12. This procedure may be understood from the following description.

The characteristic equation describing the relationship between the output V of the oxygen sensor and the O2 concentration percentage P is given by $$V = C * \ln(1-P),$$

where C is a constant.

The results of this equation with 14% offset are represented by a look-up table having a number of data points, illustrated by the following table wherein the individual values are, of course, functions of pressure, temperature and the like.

| V   | P  |
|-----|----|
| 0   | 14 |
| 28  | 15 |
| 46  | 16 |
| 65  | 17 |
| 84  | 18 |
| 103 | 19 |
| 122 | 20 |
| 142 | 21 |
| 163 | 22 |
| 184 | 23 |
| 205 | 24 |

-continued

| V | P |
|---|---|
| 206 | 25 |
| 255 | 26 |

Of course, a greater or lesser number of data points may be provided and the look-up table in accordance with available memory and other constraints.

In order to calibrate the apparatus, there is applied to sensor 12 an oxygen calibration gas having a concentration of 20.9%. Since the actual output of specific sensors used in the monitor may differ, the calibration procedures normalizes the actual output to the expected value as defined by the look-up table. Thus, upon detecting the ADC converted value of the actual sensor output as amplified by variable-gain amplifier 20, microprocessor 22 controls EEPOT 34 to change the gain of amplifier 20 in order to provide a value matching the expected output value. However, it is recognized that achieving the precise output value absolutely corresponding to the calibrated concentration is not practical. Accordingly, the method of the present invention accepts an ADC converted value ("ADC-calgas") which is in a predetermined narrow range corresponding to the calibrated gas concentration, and stores the same in order to be able to re-create the calibration of the sensor for any monitoring operation.

More specifically, assuming a nominal output from sensor 12, in accordance with the foregoing table the output value from amplifier 20 should be 141 when sensor 12 is exposed to oxygen at a concentration level of 20.9%. When the actual value differs from 141, the setting of EEPOT 34 is changed until the output of amplifier 20 attains the expected value of 141 or a value in a narrow range including 141. This may be done by adjusting the EEPOT setting upwardly at step 430, if it is determined at step 420 that the actual ADC value represents a value less than 132, and by adjusting the EEPOT setting downwardly at step 450, if it is determined at step 440 that the actual ADC value represents an output value greater than 152. As is apparent from FIG. 4, steps 420–450 are repeated until there results an ADC value representing an output from sensor 12 which is in the range of 132 to 152. Both the setting of EEPOT 34 which is required to attain the output value ADC-calgas and the value ADC-calgas obtained thereby are thus characteristics of the particular sensor used in a particular monitor.

Upon obtaining an output value in the proper range, both the ADC value ADC-calgas and the EEPOT setting are collected at step 460 and are stored at step 470. Flashing of the green LED is terminated, and normal illumination thereof begun, at step 480. Thereafter, operation returns to the flow chart of FIG. 3, to await beginning of a monitoring operation. As previously noted herein, when monitoring begins, part of the initialization is the retrieval of the EEPOT value and the ADC-calgas value stored during calibration, and restoring the gain of variable amplifier 20 to its calibrated value to permit proper indication of the oxygen concentration to which sensor 12 is exposed in operation.

The following provides an example of the procedure for obtaining the actual oxygen concentration in a monitoring operation.

During monitoring, the ADC-calgas value and the EEPOT setting, corresponding to a position of the gain potentiometer, are retrieved by the microprocessor which then sets the EEPOT 34 to the retrieved setting. A sample of the ADC value for the unknown gas concentration ("ADC-unknown") is collected. From the values provided in the above table ("TBL-calgas"), from ADC-calgas and from ADC-unknown, the scaled unknown concentration (SCALED-unknown) is obtained as follows.

Using a linear interpolation, there is first obtained the scaled unknown concentration from the following equation:

SCALED-unknown=ADC-unknown*(TBL-calgas/ADC-calgas).

Thus, where the calibration value retrieved from the non-volatile memory 24 is 134, where the unknown ADC value is 115, and where the table value for 20.9% is 141, the above equation provides that SCALED-unknown=115*(141/134)=121.

The actual oxygen concentration is then obtained by linearly interpolating between adjacent data points of the look-up table, as follows. In the above table, the value 121 is found to be between 19% and 20% oxygen concentration. The oxygen concentration being monitored is then calculated as:

02%=19+(121−103)/(122−103)=19.9%.

The above described algorithm is applicable for oxygen concentrations between 14% and 26% as provided in the table. In accordance with one embodiment of the invention, a monitor may be designed to provide indications between 15% and 25%. By using a look-up table which is greater than the operating range, such as shown in the above table, it is possible to identify that the monitored concentration is, in fact, less than 15% or greater than 25%. Thus, the displayed concentration may be clamped at a value of 14.9% for concentrations below 15% and at 25.1% for concentrations above 25%, thereby to indicate out-of-range operation.

In accordance with the above disclosure, there is thus provided both a method and apparatus for monitoring and displaying both the status and the values of different gaseous concentrations using a smaller number of calibration procedures than the values or ranges being monitored. More particularly, the invention makes it possible to display both status and concentrations over a wide range of values using only a single calibration and only a single calibration gas.

The foregoing description of the preferred embodiment of the invention has been presented for purposes of illustration and description. It is not intended to be exhaustive or to limit the invention to the precise forms disclosed, since many modifications or variations thereof are possible in light of the above teaching. For example, different forms of status displays, alarms and concentration level displays may be used. Although LED's are contemplated in accordance with the presently preferred embodiment, other displays may be used such as CRT, LCD, flat panel, gas plasma devices or any other suitable display device. Similarly, alarms may be audible or visual, or may provide other sensory stimuli to the user. Although non-volatile memory 24 is presently contemplated as being a read only memory (ROM), it is possible that other forms of storage media may be used, including magnetic or optical media and any other device suitable for the purpose herein defined.

Another example of a modification to the above description of the invention pertains to the adjustable amplifier used herein and the EEPOT used for varying the gain thereof. It is possible that, rather than amplification, there may be appropriate an attenuation of the output from a sensor which may be different in form from the type presently contemplated. Similarly, it is possible that manually or otherwise variable devices may be used for such attenuation or gain control and that, upon such manual or other variation, the variable values may be sensed and stored by the control microprocessor.

Still further, it should be recognized that the inventive concept is applicable to measurements of various characteristics associated with gases or other materials, and are not necessarily limited to measurement of concentration of oxygen which is illustrative of the inventive concept.

The foregoing and other such modifications and variations are within the scope of the invention. The embodiments described herein were chosen and described in order best to explain the principles of the invention and its practical application, thereby to enable others skilled in the art to utilize the invention in various embodiments and with various modifications as are suited to the particular use contemplated therefor. It is intended that the scope of the invention be defined by the claims appended hereto, when interpreted in accordance with the full breadth to which they are legally and equitably entitled.

What is claimed is:

1. An oxygen monitor comprising:
    a sensor for sensing oxygen concentration by providing output values indicative thereof;
    a status display representing a value of sensed oxygen concentration relative to a plurality of threshold values,
    said monitor further comprising a control processor for generating status displays for a plurality of threshold values in accordance with calibration by a single calibration gas, wherein said monitor comprises a component varying an output of said sensor, and said control processor comprises:
    calibrating means for calibrating said sensor by varying an operating parameter of said component of said monitor to a calibration value providing an output value of said sensor corresponding to a concentration of said calibration gas;
    storage means for storing said calibration value of said component; and
    retrieving means operable during a monitoring operation for retrieving said calibration value from said storage means and for setting said operating parameter of said component to said calibration value to perform the monitoring operation.

2. The oxygen monitor recited in claim 1, further comprising a concentration display for displaying concentration of oxygen being monitored thereby, said control processor controlling said concentration display to display said concentration for a plurality of ranges in accordance with said calibration by a single calibration gas.

3. The oxygen monitor recited in claim 2, wherein said monitor comprises a component varying an output of said sensor, and said control processor comprises:
    calibrating means for calibrating said sensor by varying an operating parameter of said component of said monitor to a calibration value providing an output value of said sensor within a range of values corresponding to a concentration of said calibration gas;
    storage means for storing said calibration value of said component and for storing said output value of said sensor within the range of values corresponding to the concentration of said calibration gas;
    retrieving means operable during a monitoring operation for retrieving said calibration value and said output value of said sensor from said storage means and for setting said operating parameter of said component to said calibration value to perform the monitoring operation, and
    scaling means for scaling a measured value of an unknown oxygen concentration obtained during the monitoring operation in accordance with said output value of said sensor within the range of values corresponding to the concentration of said calibration gas and for providing a scaled value of the unknown oxygen concentration.

4. The oxygen monitor recited in claim 3, wherein said storage means further stores a look-up table of nominal output values from said sensor for predetermined oxygen concentration values, and
    wherein said control processor operates for determining an oxygen concentration for the unknown oxygen concentration from an output of said sensor by interpolating between predetermined oxygen concentration values corresponding to two nominal output values in said look-up table which are respectively greater than and less than said scaled value of the unknown oxygen concentration.

5. A method for monitoring oxygen concentration comprising the steps of:
    calibrating a sensor using a single calibration gas;
    sensing an unknown oxygen concentration and providing output values indicative thereof;
    generating status displays relative to a plurality of threshold values in accordance with said calibration by said single calibration gas;
    displaying concentration of the oxygen being monitored for a plurality of ranges in accordance with said calibration by said single calibration gas;
    wherein said calibrating step comprises varying an operating parameter of a component varying an output of said sensor to obtain a calibration value corresponding to a concentration of said calibration gas;
    storing said calibration value of said component; and
    during a monitoring operation, retrieving said calibration value for setting said operating parameter of said component to said calibration value to perform the monitoring operation.

6. The oxygen monitoring method recited in claim 5, wherein said calibrating step comprises varying an operating parameter of a component varying an output of said sensor to obtain a calibration value within a range of values corresponding to a concentration of said calibration gas;
    storing said calibration value of said component and storing said calibration value of said sensor within the range of values corresponding to the concentration of said calibration gas;
    during a monitoring operation, retrieving said calibration value and said output value of said sensor for setting said operating parameter of said component to said calibration value to perform the monitoring operation, and
    scaling a measured value of an unknown oxygen concentration during the monitoring operation in accordance with said calibration value within the range of values corresponding to the concentration of said calibration gas and providing a scaled value of the unknown oxygen concentration.

7. The oxygen monitoring method recited in claim 6, wherein said step of storing further comprises storing a look-up table of nominal output values from said sensor for predetermined oxygen concentration values, and
    determining an oxygen concentration for the unknown oxygen concentration from an output of said sensor by interpolating between predetermined oxygen concentration values corresponding to two nominal output values in said look-up table which are respectively greater than and less than said scaled value of the unknown oxygen concentration.

8. A gas concentration monitor comprising:

a sensor for sensing concentration of a gas and providing output values indicative of the concentration;

a status display which provides an indication of a relationship between a value of the sensed gas concentration and a plurality of threshold values;

a control processor for generating signals to drive said status display for indicating said relationship to said plurality of threshold values in response to a calibration by a single calibration gas; and a concentration display for displaying the concentration of the gas being monitored, said control processor controlling said concentration display to display said concentration in accordance with said calibration by a single calibration gas.

9. The gas concentration monitor recited in claim 8, further comprising:

a variable gain amplifier receiving an output from said sensor and having a variable gain for scaling said output to provide a calibrated output value corresponding to a concentration of a calibration gas;

an electrically erasable potentiometer responsive to said control processor for controlling the gain of said variable gain amplifier;

a non-volatile memory connected to said control processor, to said variable gain amplifier and to said electrically erasable potentiometer;

said non-volatile memory storing a setting of said electrically erasable potentiometer used to obtain said calibrated output value from said sensor when sensing said calibration gas;

said non-volatile memory further storing an output value from said sensor when sensing said calibration gas and said electrically erasable potentiometer is adjusted to obtain said calibrated output value;

said control processor programmed for implementing a calibration procedure when said sensor senses said calibration gas by:

controlling said electrically erasable potentiometer to a setting which varies the gain of said variable-gain amplifier to obtain from said sensor an output value within a predetermined narrow range about a known concentration of said calibration gas;

controlling said non-volatile memory to store said output value within said predetermined narrow range as said calibrated output value; and controlling said non-volatile memory to store said setting of said electrically erasable potentiometer which obtains said calibrated output value.

10. The gas concentration monitor recited in claim 9, wherein said control processor is further programmed for implementing monitoring of an unknown concentration of a gas by:

retrieving said setting of said electrically erasable potentiometer and setting said electrically erasable potentiometer thereto in order to vary the gain of said variable-gain amplifier;

scaling an output value from said sensor when sensing said unknown concentration by a factor including a ratio of a known output value for said calibration gas to said calibrated output value; and performing an interpolation between two predetermined gas concentration values corresponding to two nominal output values of said sensor which are respectively greater than and less than said scaled value of the unknown gas concentration, thereby obtaining a concentration value of the gas to which said sensor is exposed.

11. The gas concentration monitor recited in claim 10, wherein said control processor is further programmed for controlling said concentration display for displaying the concentration value of the gas to which said sensor is exposed obtained by said interpolation.

12. The gas concentration monitor recited in claim 11, wherein said non-volatile memory further stores a look-up table including nominal output values of said sensor which respectively correspond to predetermined values of concentration of the gas, and said control processor is further programmed for accessing said look-up table to obtain said two predetermined gas concentration values corresponding to two nominal output values of said sensor which are respectively greater than and less than said scaled value of the unknown gas concentration.

13. The gas concentration monitor recited in claim 11, wherein said control processor is further programmed for controlling said status display to operate one of a plurality of indicators to indicate a relationship between said concentration value of the gas to which said sensor is exposed and a predetermined threshold.

14. The gas concentration monitor recited in claim 13, wherein said non-volatile memory further stores a look-up table including nominal output values of said sensor which respectively correspond to predetermined values of concentration of the gas, and said control processor is further programmed for accessing said look-up table to obtain said two predetermined gas concentration values corresponding to two nominal output values of said sensor which are respectively greater than and less than said scaled value of the unknown gas concentration.

15. The gas concentration monitor recited in claim 10, wherein said non-volatile memory further stores a look-up table including nominal output values of said sensor which respectively correspond to predetermined values of concentration of the gas, and said control processor is further programmed for accessing said look-up table to obtain said two predetermined gas concentration values corresponding to two nominal output values of said sensor which are respectively greater than and less than said scaled value of the unknown gas concentration.

16. The gas concentration monitor recited in claim 10, wherein said control processor is further programmed for controlling said status display to operate one of a plurality of indicators to indicate a relationship between said concentration value of the gas to which said sensor is exposed and a predetermined threshold.

17. An oxygen monitor comprising:

a sensor for sensing oxygen concentration by providing output values indicative thereof;

a status display representing a value of sensed oxygen concentration relative to a plurality of threshold values, said monitor further comprising a control processor for generating status displays for a plurality of threshold values in accordance with calibration by a single calibration gas, calibration display for displaying concentration of oxygen being monitored thereby, said control processor controlling said concentration display to display said concentration for a plurality of ranges in accordance with said calibration by a single calibration gas, calibrating means for calibrating said sensor by varying an operating parameter of said component of said monitor to a calibration value providing an output value of said sensor within a range of values corresponding to a concentration of said calibration gas;

storage means for storing said calibration value of said component and for storing said output value of said sensor within the range of values corresponding to the concentration of said calibration gas;

retrieving means operable during a monitoring operation for retrieving said calibration value and said output value of said sensor from said storage means and for setting said operating parameter of said component to said calibration value to perform the monitoring operation, and scaling means for scaling a measured value of an unknown oxygen concentration obtained during the monitoring operation in accordance with said output value of said sensor within the range of values corresponding to the concentration of said calibration gas and for providing a scaled value of the unknown oxygen concentration.

18. A method for monitoring oxygen concentration comprising the steps of:

calibrating a sensor using a single calibration gas;

sensing an unknown oxygen concentration and providing output values indicative thereof;

generating status displays relative to a plurality of threshold values in accordance with said calibration by said single calibration gas; and displaying concentration of the oxygen being monitored for a plurality of ranges in accordance with said calibration by said single calibration gas, wherein said calibration step comprises varying an operating parameter of a component varying an output of said sensor to obtain a calibration value within a range of values corresponding to a concentration of said calibration gas;

storing said calibration value of said component and storing said calibration value of said sensor within the range of values corresponding to the concentration of said calibration gas;

during a monitoring operation, retrieving said calibration value and said output value of said sensor for setting said operating parameter of said component to said calibration value to perform the monitoring operation, and scaling a measured value of an unknown oxygen concentration during the monitoring operation in accordance with said calibration value within the range of values corresponding to the concentration of said calibration gas and providing a scaled value of the unknown oxygen concentration.

\* \* \* \* \*